United States Patent [19]

Pellatiro

[11] Patent Number: 4,817,424
[45] Date of Patent: Apr. 4, 1989

[54] STRIP INSPECTING APPARATUS AND ASSOCIATED METHOD

[75] Inventor: Leonard P. Pellatiro, McKeesport, Pa.

[73] Assignee: Enamel Products & Planting Company, McKeesport, Pa.

[21] Appl. No.: 153,952

[22] Filed: Feb. 9, 1988

Related U.S. Application Data

[62] Division of Ser. No. 15,695, Feb. 17, 1987.

[51] Int. Cl.$^4$ .......................... B31B 1/00; B31B 49/00
[52] U.S. Cl. ........................................ 73/159; 413/69; 493/11; 493/357
[58] Field of Search .............. 73/159, 377; 250/252.1, 250/562, 559, 572; 346/76 L, 52; 413/69; 427/288; 222/105; 493/11

[56] References Cited

U.S. PATENT DOCUMENTS

| | | | |
|---|---|---|---|
| 2,246,906 | 6/1941 | Viebahn et al. | 250/41.5 |
| 2,576,043 | 11/1951 | Rendel | 346/33 |
| 2,735,329 | 2/1956 | Meunier | 73/159 X |
| 2,896,196 | 7/1959 | Hartford et al. | 73/159 X |
| 2,930,228 | 3/1960 | Lawrence et al. | 73/159 |
| 3,188,478 | 6/1965 | Binks | 250/219 |
| 3,269,178 | 8/1966 | Kohler | 73/159 |
| 3,349,611 | 10/1967 | Benjamin et al. | 73/159 |
| 3,445,672 | 5/1969 | Marks | 250/219 |
| 3,500,437 | 3/1970 | Foerster | 346/106 |
| 3,619,578 | 11/1971 | George | 235/92 V |
| 3,633,211 | 1/1972 | Batzdorff | 346/14 |
| 3,700,909 | 10/1972 | Murray et al. | 250/219 DF |
| 3,991,663 | 11/1976 | Glasby | 493/11 |
| 4,004,152 | 1/1977 | Obser et al. | 250/159 |
| 4,204,012 | 5/1980 | Brocklehurst et al. | 118/42 |
| 4,209,120 | 6/1980 | Ruegg et al. | 226/32 |
| 4,229,645 | 10/1980 | Vigano et al. | 235/92 |
| 4,304,981 | 12/1981 | Gappa | 346/76 L X |
| 4,306,808 | 12/1981 | Vander Neut | 356/239 |
| 4,329,377 | 5/1982 | Voelker et al. | 427/9 |
| 4,514,436 | 4/1985 | Moerschel | 427/10 |
| 4,578,052 | 3/1986 | Engel et al. | 493/11 |
| 4,650,447 | 3/1987 | Meschi | 493/11 |
| 4,652,329 | 3/1987 | Focke | 156/351 |

Primary Examiner—Daniel M. Yasich
Attorney, Agent, or Firm—Arnold B. Silverman

[57] ABSTRACT

Apparatus for inspecting strip including metal strip includes inspection elements for monitoring a plurality of properties of the strip, a transport unit for passing the strip by the inspection elements and signal generators on the inspection elements for emitting a signal to a strip processing unit which emits a signal to a strip marking unit when one or more properties departs from predetermined limits. The strip marking system provides markings in one or more of a plurality of longitudinal zones on the strip responsive to signals indicating that one or more properties have departed from the desired limits with the particular zone identifying the particular property. A strip edge detector determines the edge of the strip and an actuator positions the marking unit in the desired transverse position relative to the strip so as to establish the zones where desired. The system may provide a printout identifying undesired properties and the particular longitudinal section of the strip where these appear. A method of inspecting strip exemplified by the apparatus is also provided.

6 Claims, 6 Drawing Sheets

STRIP INSPECTING APPARATUS AND ASSOCIATED METHOD

This is a division of application Ser. No. 07/015,695, filed Feb. 17, 1987.

BACKGROUND OF THE INVENTION

1. Field of the Invention

The present invention relates to apparatus and an associated method for providing indicia on a strip identifying specific properties which depart from predetermined ranges.

2. Description of the Prior Art

It has been known to employ metal sheet to fabricate various types of products. It has also been known to inspect such sheets to make sure that the properties are within desired limits.

For certain uses such as metal cans, organic coatings are generally applied on sheets and the integrity and thickness of such coatings as well as other properties have been monitored.

Where sheets were provided in individual web form it was relatively easy to discard a particular web where defects were found. One of the problems with employing webs is that the speed which is achievable in using metal strip provided on large coils for continuous processing cannot be obtained.

It has been known to provide means for marking defective zones of metal webs and strip as well as other materials in order to provide an indication as to what portions are defective within a particular set of specifications. See, generally, U.S. Pat. Nos. 2,246,906; 2,576,043; 3,500,437; 3,188,478; 3,633,211; and 4,514,436.

U.S. Pat. No. 2,930,228 discloses a system for inspecting a coiled metal strip for various defects and placing markings corresponding to defects within certain zones on an associated tape.

U.S. Pat. No. 3,455,672 discloses a system for inspecting defects in glass and providing corresponding markings on the glass within the zones where the defects exist.

U.S. Pat. No. 3,619,578 discloses an inspection device for detecting depressions in softwood veneer by providing a light source, an associated plate member and a sensor monitoring for light passing between the plate member and the veneer.

In spite of these previously known systems, there remains a very real and substantial need for a strip detecting device which will simultaneously provide an indication on the strip in the region where a property defect exists of departures from desired properties and identification of the specific property.

SUMMARY OF THE INVENTION

The present invention has met the hereinbefore described need by providing an apparatus and associated method which will facilitate enhanced efficiency of inspection of a metal strip.

The apparatus of the present invention includes strip supply means for providing said metal strip, inspection means for monitoring a plurality of properties of the strip, and transport means for passing the strip by said inspection means. The inspection means have signal generating means for emitting signals related to the properties being monitored. Signal processing means receive the signals and emit a responsive error signal when there is a departure from predetermined properties. Strip marking means provide markings in one or more of a plurality of longitudinal zones on the strip responsive to the error signals with each zone representing a particular type of defect and the markings being placed within the longitudinal section wherein the defect exists.

In a preferred embodiment a plurality of marking elements are provided as a unit and are adapted to be positioned in a predetermined position with respect to the longitudinal zones by actuator means which cooperate with strip edge detecting means.

A method of inspecting metal may provide the inspection means for monitoring a plurality of strip properties and emitting signals responsive thereto, marking the strip in a plurality of longitudinal zones each related to a particular strip property when a defect exists and effecting the marking within a transverse zone of the strip where the position of the strip edge is preferably monitored and the marking means positioned so as to align the marking elements with the longitudinal zones.

It is preferred to provide metal fabricating equipment which receives the sheet or strip from the marked coil and to have mark decoders monitoring the strip so that as the strip progresses through the metal fabricating equipment, an operator can determine what defects exist within what regions and, if desired, allow those regions to be eliminated or passed through the metal fabricating equipment without fabricating products, thereby enhancing the efficiency of the operation.

It is an object of the present invention to provide apparatus and an associated method for inspecting metal strip which may be provided in coil form and marking the strip when the property limits have been exceeded along predetermined longitudinal zones each of which represent a particular property of the strip.

It is a further object of the present invention to provide such an apparatus and method which facilitates providing the zone marking within the longitudinal section of the strip wherein the property defect exists.

It is a further object of the present invention to provide such a system wherein such marking may be effected automatically and precisely in an economical and efficient manner.

It is yet another object of the present invention to provide such a system wherein a mark decoder may be provided on subsequent fabricating equipment so as to facilitate obtaining the benefit of the previously marked defective strip areas.

It is yet another object of the present invention to provide a system which is capable of creating a printout which lists which defects are present in a strip and the longitudinal position at which the defects occur.

These and other objects of the invention will be more fully understood from the following description of the invention on reference to the illustrations appended hereto.

DESCRIPTION OF THE PREFERRED EMBODIMENTS

It will be appreciated that the present invention is usable with a wide variety of strip products which may advantageously be presented in coil form. In general, a plurality of properties of the strip will be monitored simultaneously in an automated form and the sheet marked so as to give a tangible indication as to where a defect exists and the nature of the defect. Among the sorts of properties which might be monitored, for example, on a steel strip having a tin or galvanized coating and an organic coating on one surface would be variations in thickness of the sheet, variations in thickness of the coatings, the presence of undesired pin holes in the sheets, defects in the welds which are frequently used to secure together adjacent longitudinal sections of the coil, and surface defects such as scale, laminations and mill marks, for example.

Figure 1:
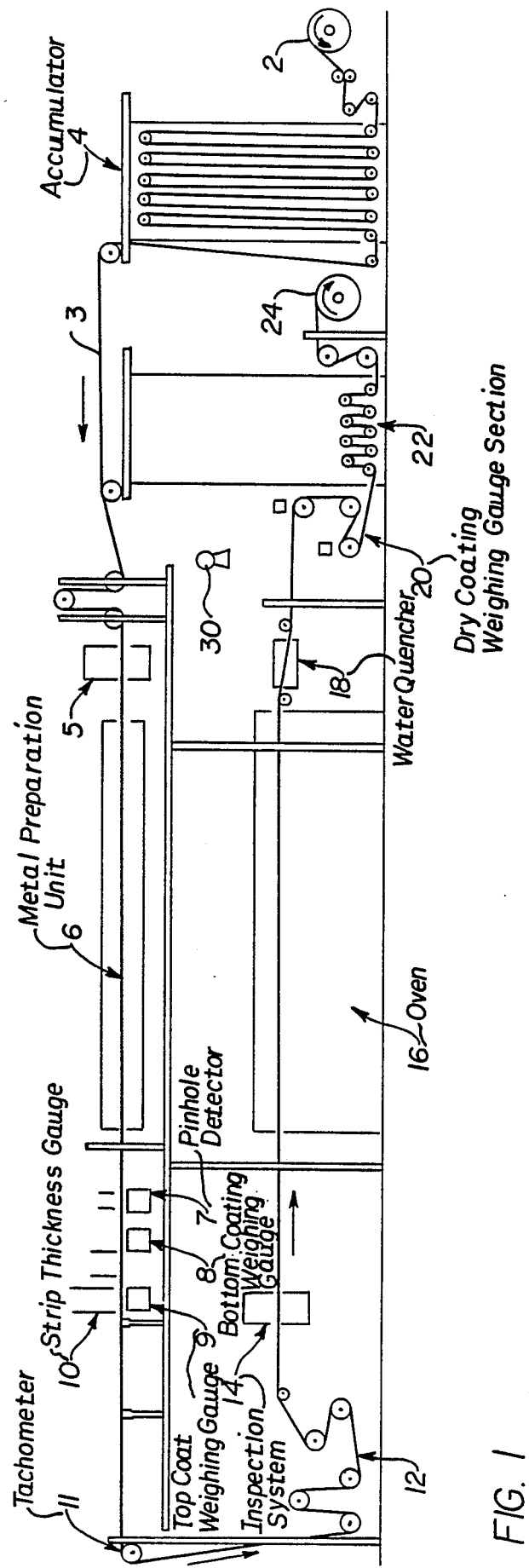
FIG. 1 is a schematic illustration of a form of metal strip processing apparatus within which the present invention may be employed.

Referring now in greater detail to FIG. 1, there is shown a form of metal strip processing system in which the present invention may be usable. A coil of metal strip 2 is positioned on a suitable uncoiler and is paid out and advances through an accumulator 4 which may be of a conventional type and have a predetermined number of rolls so as to provide for accumulation of the desired length of strip. The strip 3 passes through a weld detection unit 5 which is employed to track coil sequencing through the process. The strip 3 then passes through a metal preparation unit 6 within which the strip may be subjected to conventional cleaning and metal treatment operations.

As the strip 3 continues to advance in the direction indicated by the arrows, it passes through a series of inspection devices, which may be of a conventional variety. Shown for purposes of illustration are a pin hole detector 7, a bottom coating weight gauge 8, a top coating weight gauge 9 and a total strip thickness gauge 10. It will be appreciated that other sorts of property monitoring devices may be provided at this point such as a weld integrity gauge or surface inspection gauges, for example.

In the upper left-hand portion of the apparatus there is shown a tachometer 11. This unit provides references for tracking coil to coil identity as well as locations of defects as determined by inspection devices within each coil.

Downstream of the tachometer 11 is the organic coating applicator unit 12 which provides the organic coating on one or both surfaces of the strip 3. After passing through the organic organic coating applicator unit 12, the strip passes through an inspection device 14 which provides an indication of the wet film gauge of the organic coating applied by organic coating applicator unit 12. By means of a servo system (not shown) feedback to the coder is provided from the inspection system 14 as well as other feedback. The strip 3 then passes through an oven which cures the organic coating applied at organic coating applicator unit 12. After emerging from the oven 16, the strip passes through a water quench 18 in order to reduce the temperature of the coated strip. At station 20 there is provided a dry coating weight gauge to monitor the dry gauge of the organic coating applied in organic coating applicator unit 12. A servomechanism providing feedback to organic coating applicator unit 12 regarding this inspection is also provided If desired, an inspector 30 or automated surface inspection system may monitor the strip and visually inspect the same with the ability to take desired action should he or she perceive that the organic coating is defective. The marking unit of the present invention is preferably introduced to the system at this location with or without the presence of the observer 30. After emerging from the marking station, the coil passes through an additional accumulator 22 and then is wound on to takeup reel 24.

With this background, the details of the preferred embodiments of the invention will be considered.

Figure 2:
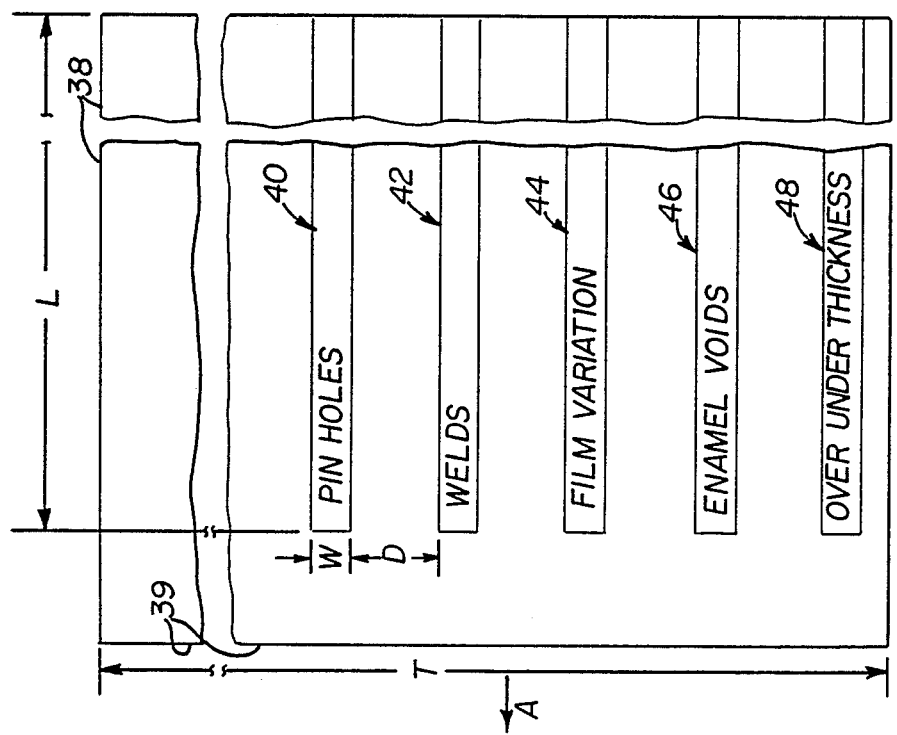
FIG. 2 is a schematic illustration in plan of a portion of a strip which may be processed by the present invention.
Figure 4:
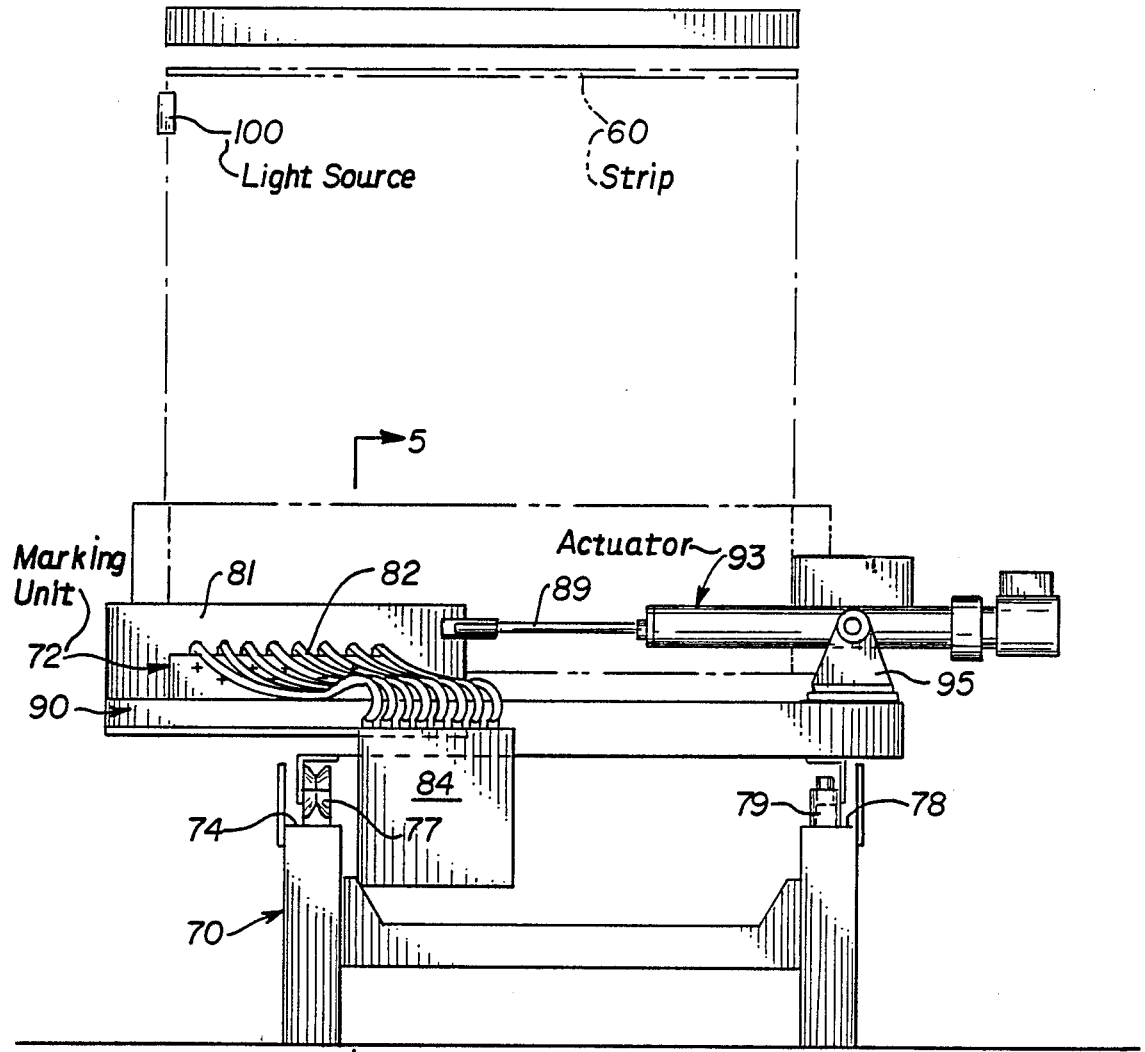
FIG. 4 is a rear elevational view of the apparatus shown in FIG. 3.

Referring to FIG. 2, there is shown a strip section 38 of a piece of strip having a lead edge 39 travelling in the direction indicated by the arrow A. Considering a transverse sector of the strip of length L, the marking system of the present invention will employ a series of spaced, generally parallel longitudinal zones of width W, such as zones 40, 42, 44, 46, 48. It is contemplated that each of these zones will represent a specific property. For example, zone 40 may represent pin holes. Should a pin hole defect occur within the zone of length L anywhere across the width T of the strip, a mark will be placed within zone 40. As a result, one examining the strip will be informed that a pin hole, is present within the zone of length L somewhere within width T of the strip. Similarly, zone 42 may be employed for weld defects, zone 44 may be used for variations in organic film thickness, zone 46 may be employed for pin holes in the organic coating and zone 48 may be used for metal strip being over or under the desired gauge thickness.

By way of example, the strip may have a width T of about 30 to 36 inches with the width of the longitudinal zones 40-48, with W being about 2 inches and the space between adjacent longitudinal zones D being about 0.1 to 5 inches.

If desired, in addition to indicating which zone L contains a particular property defect as by marking zone 44, the longitudinal zones may be subdivided into smaller units such that position within the width W of the marking in zone 40, for example, would indicate which quadrant of the full transverse width T of the strip contains the particular defect. This may readily be accomplished by means known to those skilled in the art as by modifying the computer output signals to reflect this refinement and providing additional responsive marking means to provide markings within desired transverse portions of the longitudinal zones.

Figure 3:
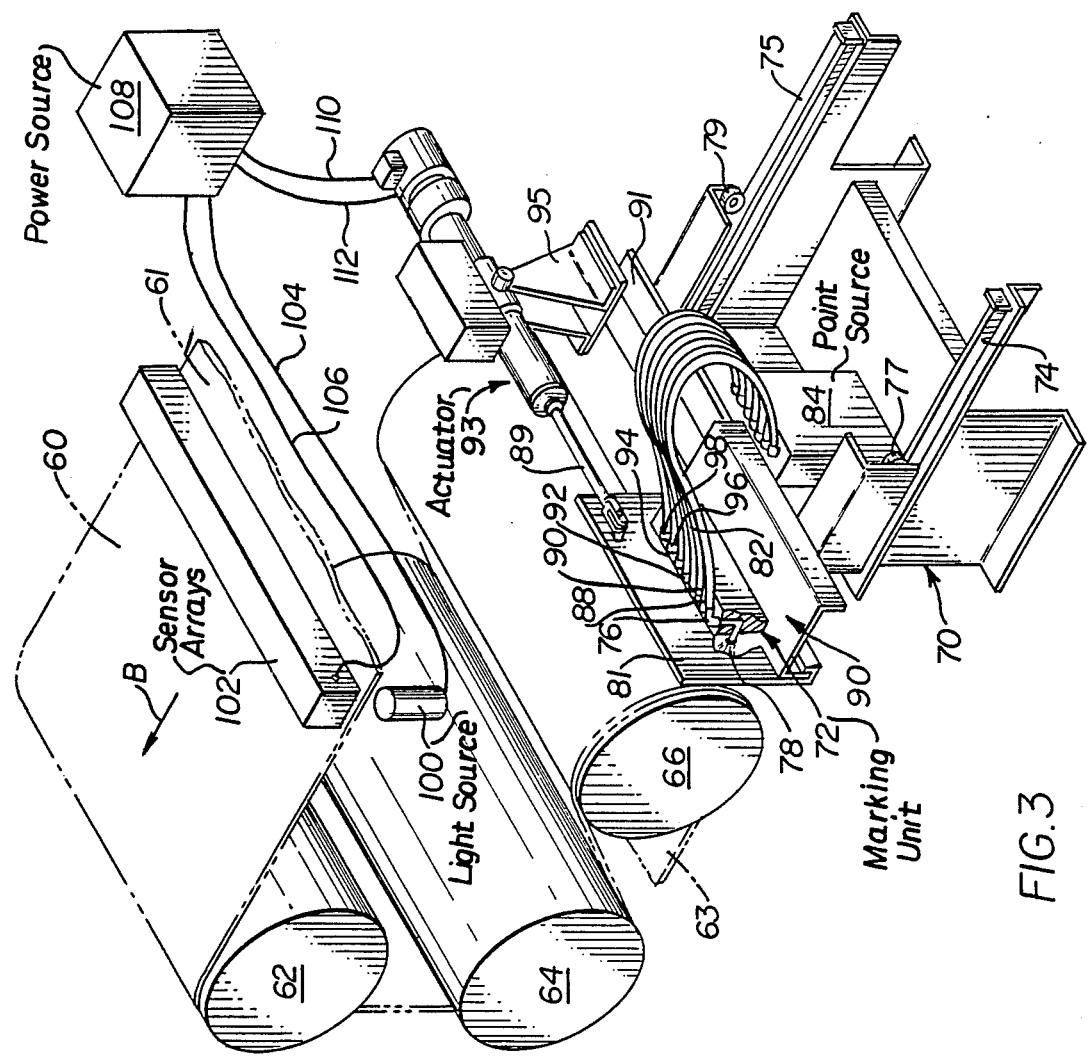
FIG. 3 is a perspective view showing a portion of the sensing and marking apparatus of the present invention.

Referring to FIGS. 3 through 7, additional details of the manner in which the strip position and the position of the longitudinal zones 40-48 are maintained with the desired precision in relationship to the strip edges will now be considered. Referring in greater detail to these figures, it i seen that a strip 60 having trailing portion 61, as shown in FIG. 3, passes through the marking section of the equipment in a direction indicated by arrow B, passes over guide rolls 62, 64 and then around guide roll 66 with the leading edge 63 emerging therefrom. The marking station has a foundation 70 with the marking unit 72 providing a plurality of marker dispensing outlets. Marker dispenser 76 has an outlet 78 and a hose 82 connecting it with a source 84 of the material to be deposited, such as paint, for example. Similarly, the additional marking elements 88, 90, 92, 94, 96, 98 are positioned in relative transverse spaced relationship preferably with substantially equal spacing between adjacent discharge nozzles which spacing corresponds to the center-to-center spacing of the longitudinal zones 40–48 on the metal strip.

In a preferred embodiment, a pair of rails 74, 75, support the wheeled carriages 77, 79 on which the marking unit 72 is mounted to permit relative movement between the marked unit and roll 66.

Marking unit 72 has adjacent plate portion 81 which is fixedly secured to the base of support 90. Actuator 93 which may preferably be a linear actuator has a projecting piston rod 89 which is secured to plate 81. It will be appreciated that as the rod 94 reciprocates, the plate 81 and the marking unit 72 will be subjected to relative transverse movement with respect to the longitudinal direction of the strip. In this manner, the marking unit may be moved with respect to the strip edge. It is noted that the actuator 93 is secured to base 95 which in turn is supported on element 91.

In order to effect a precise determination regarding the position of the edge of strip 60 an edge sensor is provided. In the form shown, the sensor consists of a light source 100 and an array of sensors 102. (A suitable edge detector is that sold by North American Manufacturing Co. of Cleveland, Ohio.) By determining what portions of the sensors are receiving light one may determine the precise position of the strip edge. By knowing the precise position of the strip edge, and knowing the positions of the marking unit dispensing nozzles such as 78, one may precisely position the marking dispensers within the desired longitudinal zones which are to be marked. A source of electrical power 108 energizes light source 100 through lead 104 and receives feedback from the sensor arrays 102 through lead 106. Through relays in the power source 108 the linear actuator 93 is operated through leads 110, 112 to precisely position the marking unit. A suitable linear actuator is that sold by Rayco International, Inc. of Bethel Park, Pa. It will be appreciated that in this manner when the width of the strip being processed is changed, or the position of the same on the rolls is changed, one may easily effect proper indexing of the marking units with respect to the desired longitudinal zones. It will be understood that the zones are preferably not physically defined on the strip, however, the markings which are applied will appear within the respective zones. It will be appreciated that hydraulic cylinders or other means for positioning the marking unit 72 may be employed in lieu of linear actuator 93.

Figure 5:
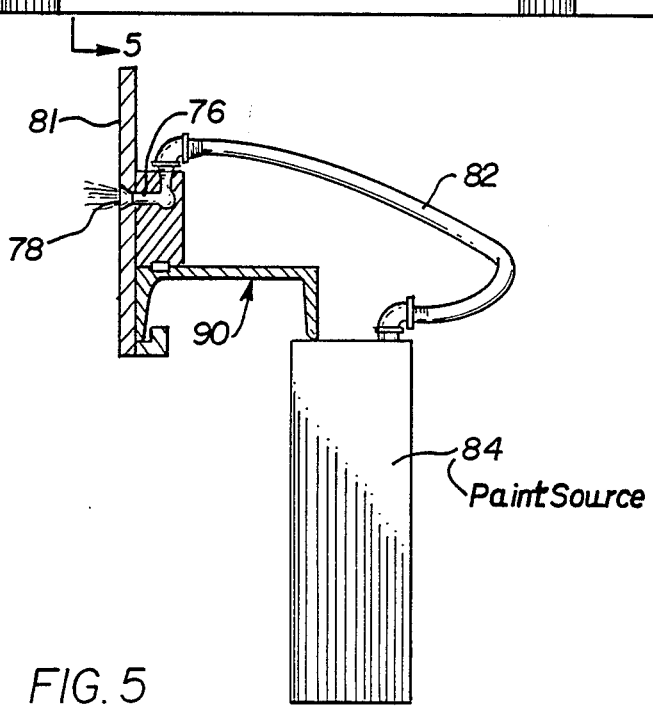
FIG. 5 is a cross-sectional illustration of a portion of the apparatus taken through 5—5 of FIG. 4.
Figure 6:
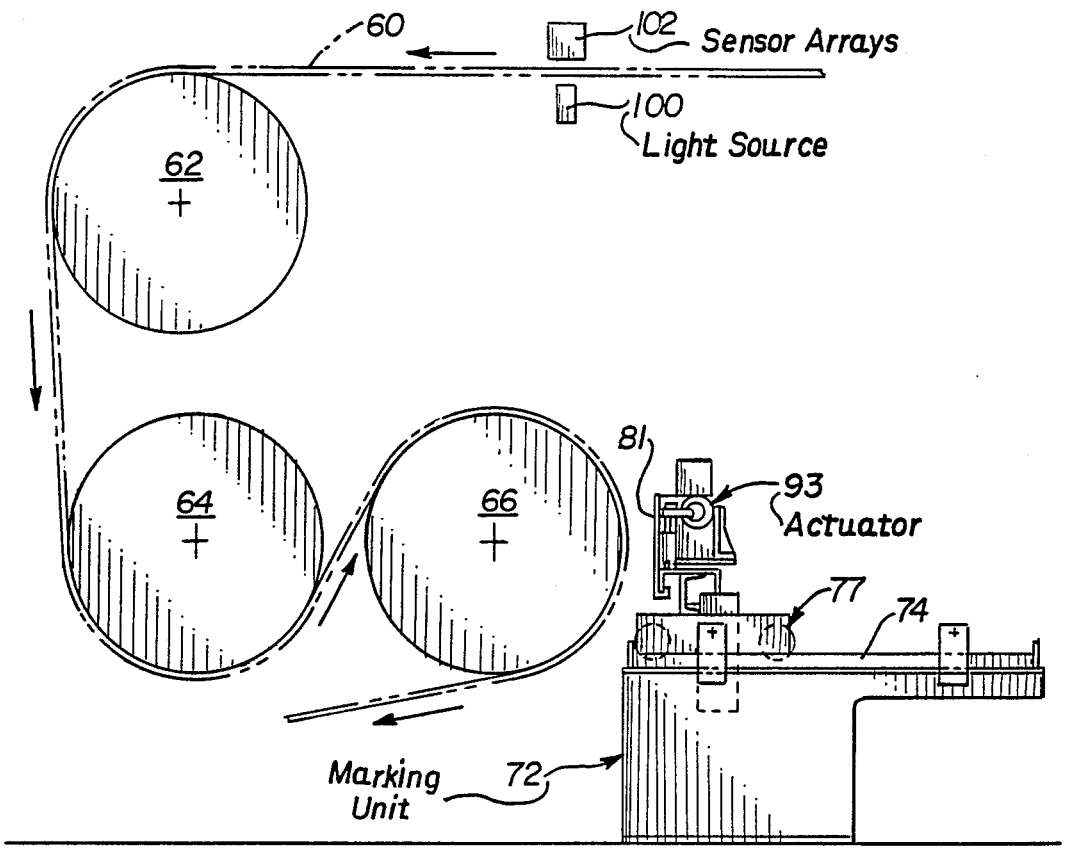
FIG. 6 is a left side elevation of the apparatus shown in FIG. 4.
Figure 7:
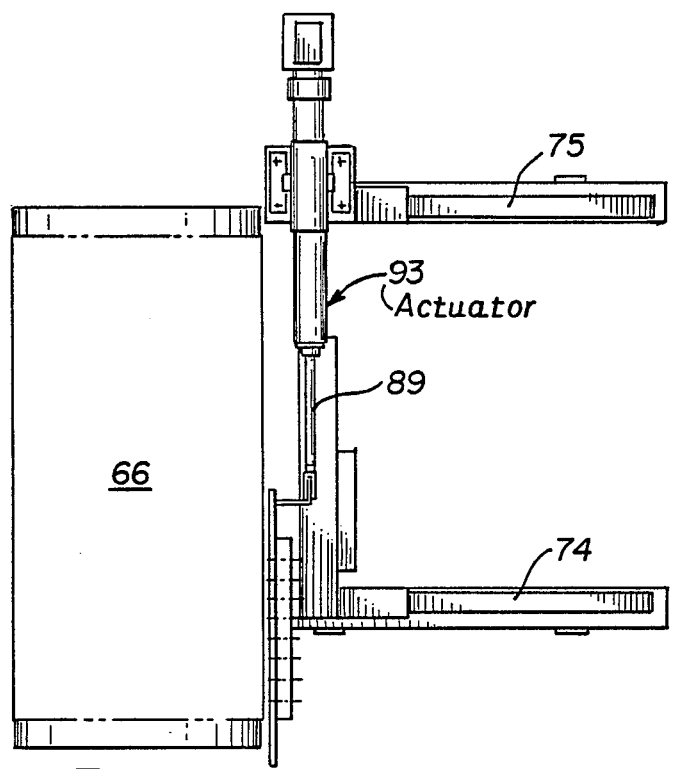
FIG. 7 is a top plan view of the apparatus shown in FIG. 4.

FIG. 5 shows schematically the interrelationship between the marking unit 72, the paint reservoir 84 and one of the discharge nozzles 78.

Figure 8:
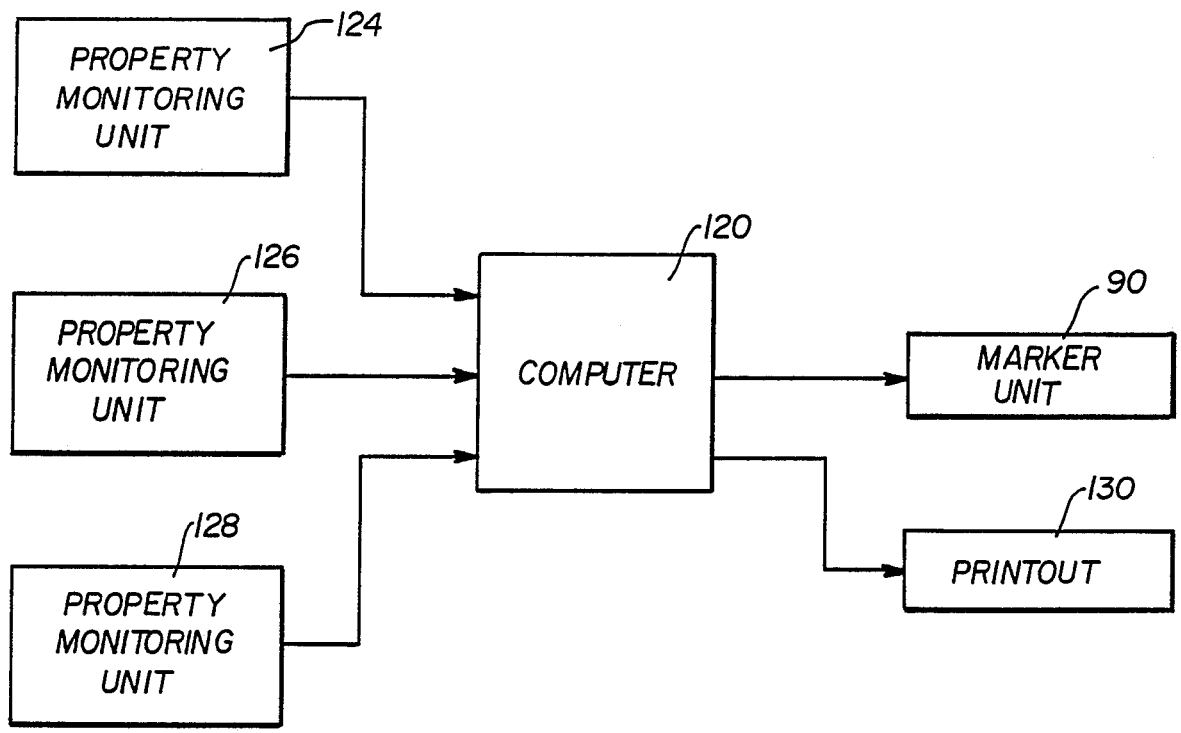
FIG. 8 is a schematic flow diagram representative of a portion of the apparatus and method of the present invention.

Referring to FIG. 8 there is shown schematically a manner in which the apparatus may be operated, although numerous ways of controlling and coordinating operation of the same will be readily apparent to those skilled in the art. The computer 120 will receive signals from a plurality of inspection units 124, 126, 128 which may be inspection devices such as those described hereinbefore in connection with FIG. 1 or other devices depending upon the number and identity of properties which are being measured. The inspection devices 124, 126, 128 will send signals, preferably on a very frequent basis, to the computer which in turn will compare the signals with the predetermined allowable values for the property being monitored. When the desired range of property values has been departed from, the computer will emit an error signal to the marking unit 90 which will then cause the particular nozzle which deposits material in the longitudinal zone related to that property to deposit paint or other suitable marking material on the longitudinal zone within the particular sector L where the defect exists. It will be appreciated that the length of the line within sector L will correspond to the length of the particular section wherein the defect occurs. For example, if a coating defect of one-eighth of an inch exists, a mark of one length would be applied the the zone at that location and if the defect were of an inch, the marking applied would be substantially longer.

The computer 120 may also advantageously provide a printout 130 which contains a matrix identifying which property defects exist and at what longitudinal positions within the coil they exist. This printout may advantageously be employed when the coil is subjected to fabrication of products therefrom.

Figure 9:
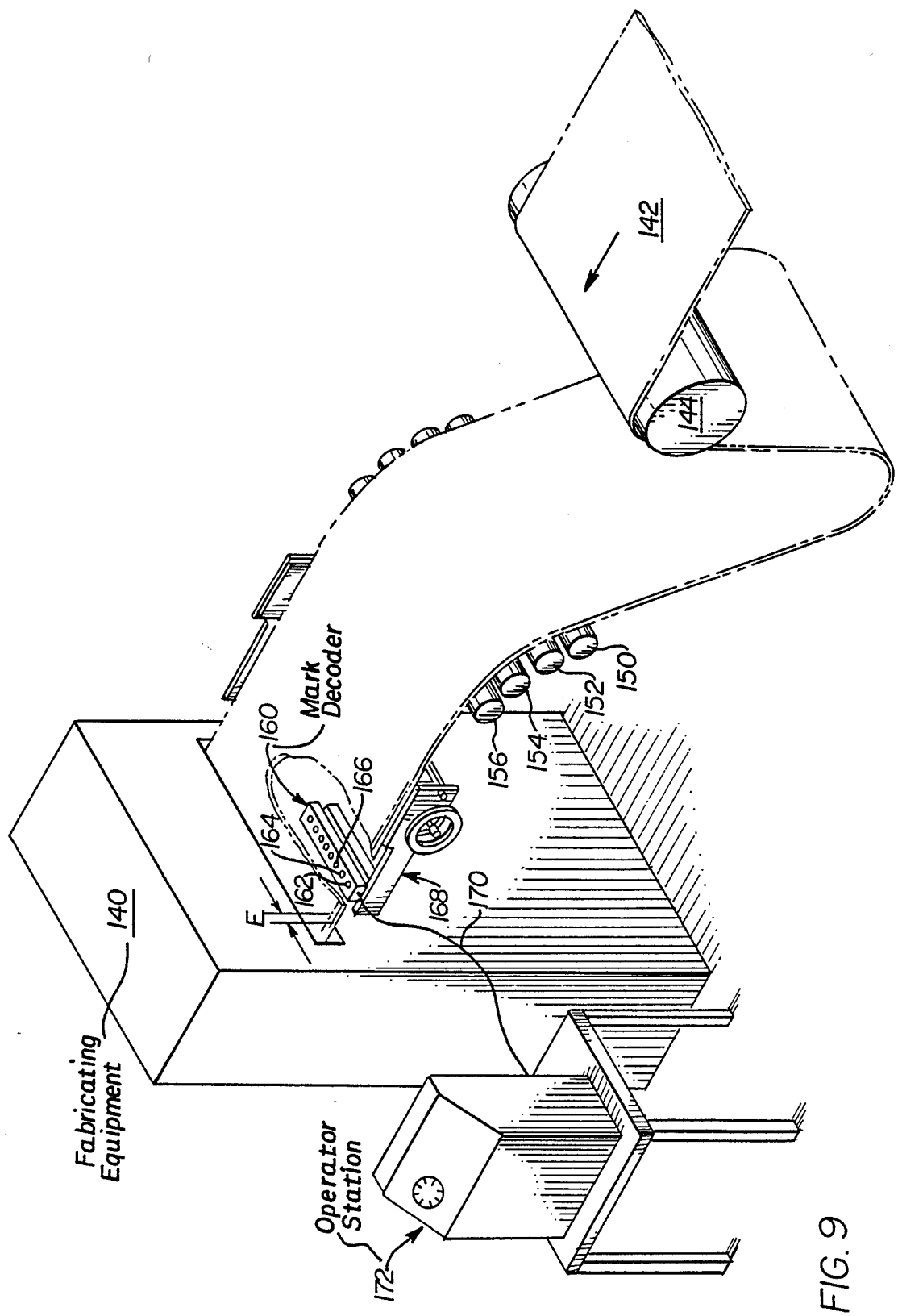
FIG. 9 is a perspective, partially schematic view showing subsequent processing of the marked strip.

Referring to FIG. 9, there is shown a piece of strip fabricating equipment which may be any suitable equipment for converting the strip into fabricated (or semifabricated) products. As a result of the premarking of the strips, with or without the printout, the user of the coil may make more efficient use of the same by minimizing or eliminating the use of areas having property defects. The strip 142 passes over support roll 144 and support rolls 150, 152, 154 and 156. Positioned upstream of the fabricating equipment 140 is a mark decoder 160 which is adapted to "read" markings on the strip indicating particular defects. A series of transversely spaced sensors such as 162, 164, 166 are positioned at transverse positions corresponding to the location of the longitudinal zones on the strip. The space between the center of the first sensor 162 and the adjacent edge of the strip is E which will correspond with the spacing between the edge of the strip and the center of the first longitudinal zone such as 48. The strip is supported by side guide 68. A suitable mark decoder may be of the type sold under the trade designation Dolan-Jenner Led-Pak Infrared decoder by Dolan-Jenner of Woburn, Mass. An operator station 172 is connected to the mark decoder 160 by lead 170 and is adapted to provide the operator of the equipment 140 with an indication of the property profile of the strip portion about to enter the equipment. If desired, a portion of the strip which is defective may either be severed from the strip prior to introduction of the strip into the equipment 140 as by shearing means (not shown) or the equipment may be turned off to permit the marked strip section to pass therethrough without the product being made therefrom.

While for purposes of clarity of disclosure, the preferred use of paint or ink as the marking material has been disclosed, it will be appreciated that other materials which will provide for precisely positioned marking which will be sufficiently durable to accomplish the objectives of the invention may be employed. Also, while it is preferred to employ a marking system which involves guns for dispensing the marking material without having this portion of the marking equipment in contact with the strip, if desired, other forms of marking means may be provided.

It will be appreciated, therefore, that the present invention has provided a efficient automatic means for effectively marking a strip so as to provide a visual indication of where in the strip property defects exist and the specific nature of the defects. All of this is accomplished in an efficient, automated manner and facilitates subsequent use of the coil in the production of products therefrom.

While as disclosed herein, in a preferred practice of the invention use in connection with inspection of metal strip is contemplated, it will be appreciated that the invention is not so limited and use in connection with other materials such as plastic or paper, for example, is contemplated.

Whereas particular embodiments of the invention have been described above for purposes of illustration, it will be evident to those skilled in the art that numerous variations of the details may be made without departing from the invention as defined in the appended claims.

I claim:

1. Apparatus for inspecting strip including strip supply means for providing said strip, inspection means for monitoring a plurality of properties of said strip,
   transport means for passing said strip by said inspection means,
   said inspection means having signal generating means for emitting signals related to the properties being monitored when said strip passes thereby,
   signal processing means for receiving said signals and emitting a responsive error signal when one of said properties in a portion of said strip departs from predetermined property limits,
   strip marking means for providing markings in one or more of a plurality of longitudinal zones on said strip responsive to said error signals with each said zone representing a particular type of defect and said markings being placed within the longitudinal section of said strip wherein said defect exists,
   fabricating equipment for converting the marked strip into fabricated products,
   feed means for feeding said marked strip into said fabricating equipment, and
   mark decoder means for providing an indication of what defects exist in portions of the strip passing adjacent thereto.

2. The strip inspection apparatus of claim 1 including
   said strip being metal strip, and
   said mark decoder having a control unit to provide an indication of said defected to an operator.

3. The metal strip inspection apparatus of claim 2 including
   said metal fabricating equipment includes can making equipment.

4. A method of inspecting strip including
   providing inspection means for monitoring a plurality of strip properties and emitting signals responsive to departures in said strip properties from predetermined levels,
   marking said strip in a plurality of longitudinal zones each related to a particular strip property when a defect in said property exists,
   effecting said marking within a section of said strip wherein said defects in strip properties exist,
   providing metal strip as said strip,
   providing means for effecting said marking,
   determining the position of an edge of said strip,
   positioning said marking means with respect to said strip edge so as to provide said stripped zones in the desired locations,
   providing marking means for effecting said marking,
   determining the position of an edge of said strip,
   positioning said marking means with respect to said strip edge so as to provide said strip zones in the desired locations,
   effecting said marking by means extending in a direction generally transverse to the longitudinal extent of said strip,
   providing metal fabricating equipment for converting said marked strip into fabricated products,
   feeding said marked strip to said equipment, and
   monitoring the markings on said strip prior to introduction of said strip into said equipment to determine what defects exist and in what portions of said strip.

5. The method of inspecting metal strip of claim 4 including
   passing portions of said strip within which said defects exist through said metal fabricating equipment without fabricating products therefrom.

6. The method of inspecting metal strip of claim 5 including
   fabricating metal cans from at least portions of said strip.

* * * * *

UNITED STATES PATENT AND TRADEMARK OFFICE
CERTIFICATE OF CORRECTION

PATENT NO. : 4,817,424

DATED : April 4, 1989

INVENTOR(S) : LEONARD P. PELLATIRO

It is certified that error appears in the above-identified patent and that said Letters Patent is hereby corrected as shown below:

On the Title Page, the Assignee's name is misspelled and should be --Enamel Products & Plating Company--.

Col. 4, line 12, a period --.-- should be inserted after "provided".

Col. 4, line 37, the comma after "hole" should be omitted.

Col. 4, line 66, "it i" should be --it is--.

Claim 2, col. 8, line 4, "defected" should be --defects--.

Signed and Sealed this

Fourteenth Day of November, 1989

Attest:

JEFFREY M. SAMUELS

Attesting Officer     Acting Commissioner of Patents and Trademarks